United States Patent [19]

Pomerantzeff

[11] 4,397,310

[45] Aug. 9, 1983

[54] ANASTIGMATIC HIGH MAGNIFICATION, WIDE-ANGLE BINOCULAR INDIRECT ATTACHMENT FOR LASER PHOTOCOAGULATOR

[75] Inventor: Oleg Pomerantzeff, Brookline, Mass.

[73] Assignee: The Government of the United States of America as represented by the Secretary of Department of Health and Human Services, Washington, D.C.

[21] Appl. No.: 239,015

[22] Filed: Feb. 27, 1981

[51] Int. Cl.³ .................................. A61B 17/36
[52] U.S. Cl. ...................... 128/303.1; 128/395; 219/121 L; 372/6; 372/109
[58] Field of Search ............ 128/303.1, 305, 395–396, 128/303 R, 397–398; 350/20, 33; 331/DIG. 1, 94.5; 219/121 L, 121 LM; 372/6, 109

[56] References Cited

U.S. PATENT DOCUMENTS

| | | | |
|---|---|---|---|
| 2,930,379 | 3/1960 | Dopp et al. | 128/396 |
| 3,096,767 | 7/1963 | Gresser et al. | 128/395 |
| 3,348,547 | 10/1967 | Kavanagh | 128/395 |
| 3,456,651 | 7/1969 | Smart | 128/303.1 |
| 3,467,099 | 9/1969 | Lotmar | 128/303.1 |
| 3,487,835 | 1/1970 | Koester et al. | 128/303.1 |
| 3,653,384 | 4/1972 | Swope | 128/303.1 |
| 3,720,213 | 3/1973 | Hobart | 128/395 |
| 3,783,874 | 1/1974 | Koester et al. | 128/303.1 |
| 3,809,092 | 5/1974 | Abraham | 128/305 |
| 3,828,788 | 8/1974 | Krasnov et al. | 128/303.1 |
| 3,906,953 | 9/1975 | Wallace et al. | 128/303.1 |
| 3,930,504 | 1/1976 | de Laforcade | 128/303.1 |
| 3,982,541 | 9/1976 | L'Esperance, Jr. | 128/303.1 |
| 4,144,888 | 3/1979 | Malyshev et al. | 128/303.1 |
| 4,174,154 | 11/1979 | Kawasaki | 128/303.1 X |
| 4,289,378 | 9/1981 | Remy et al. | 128/303.1 X |

OTHER PUBLICATIONS

Klein, Miles V.; *Optics;* John Wiley and Sons, Inc., New York, 1970, pp. 80–81.
Hausmann et al.; *Physics;* D. Van Nostrand Company, Inc., New York, 1948, p. 681.

*Primary Examiner*—Lee S. Cohen
*Assistant Examiner*—Angela D. Sykes
*Attorney, Agent, or Firm*—Holman & Stern

[57] ABSTRACT

An improved method and apparatus for photocoagulation of the fundus of a patient's eye eliminates the contact lens and provides for binocular viewing. The technique is characterized by the utilization of a common ophthalmoscopic lens for each of the illumination beam, the observation beam, and the laser beam. A scanning mirror for the laser beam is disposed on the optical axis and is rotatable in two dimensions about a fixed point which is conjugated with the nodal point of the patient's eye with respect to the ophthalmoscopic lens. The binocular viewing paths are converged onto a point on the optical axis in the plane of the first aerial image of the fundus provided by the ophthalmoscopic lens; the laser beam reflected by the scanning mirror is also focused onto that point.

14 Claims, 5 Drawing Figures

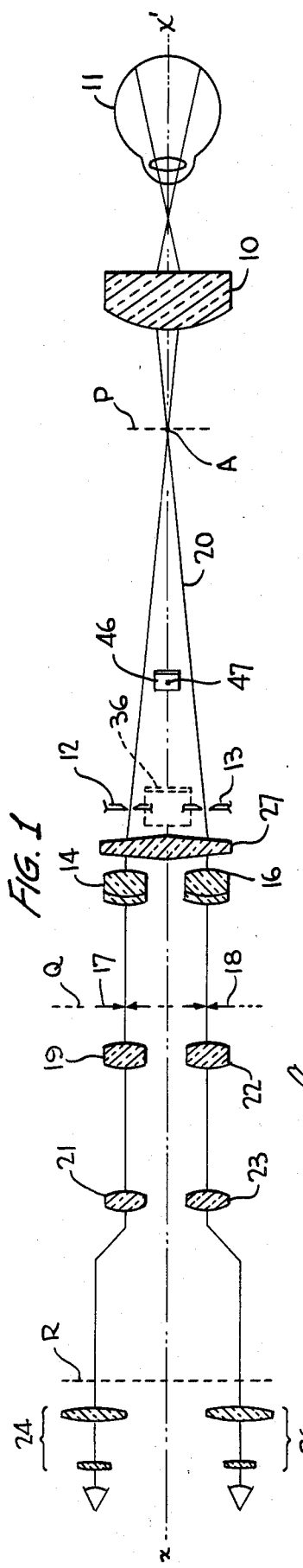
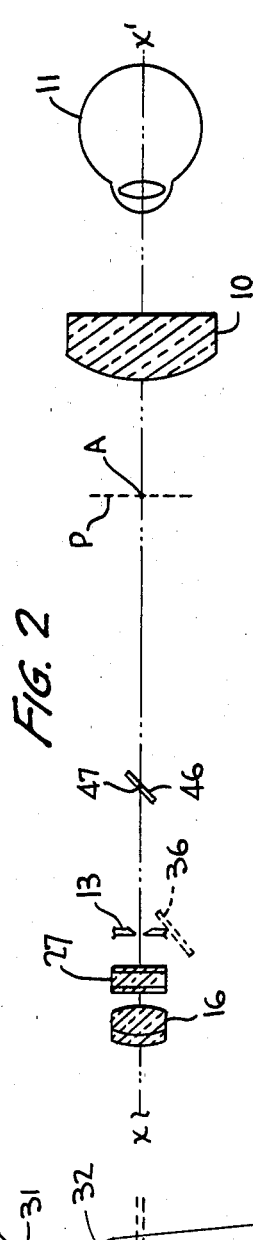
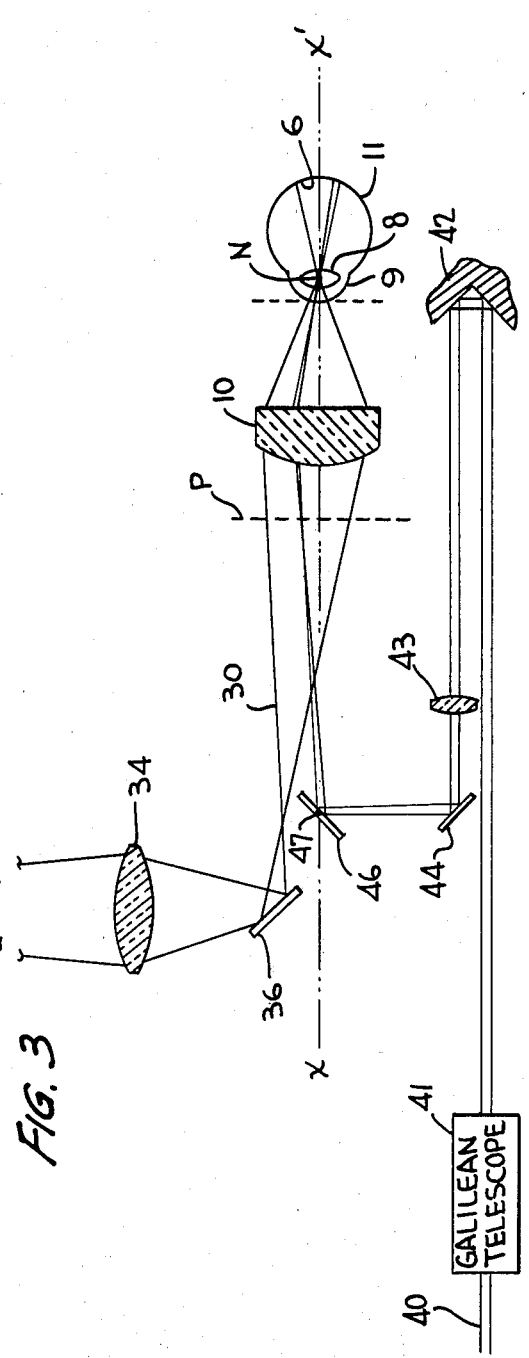
FIG. 1
FIG. 2
FIG. 3

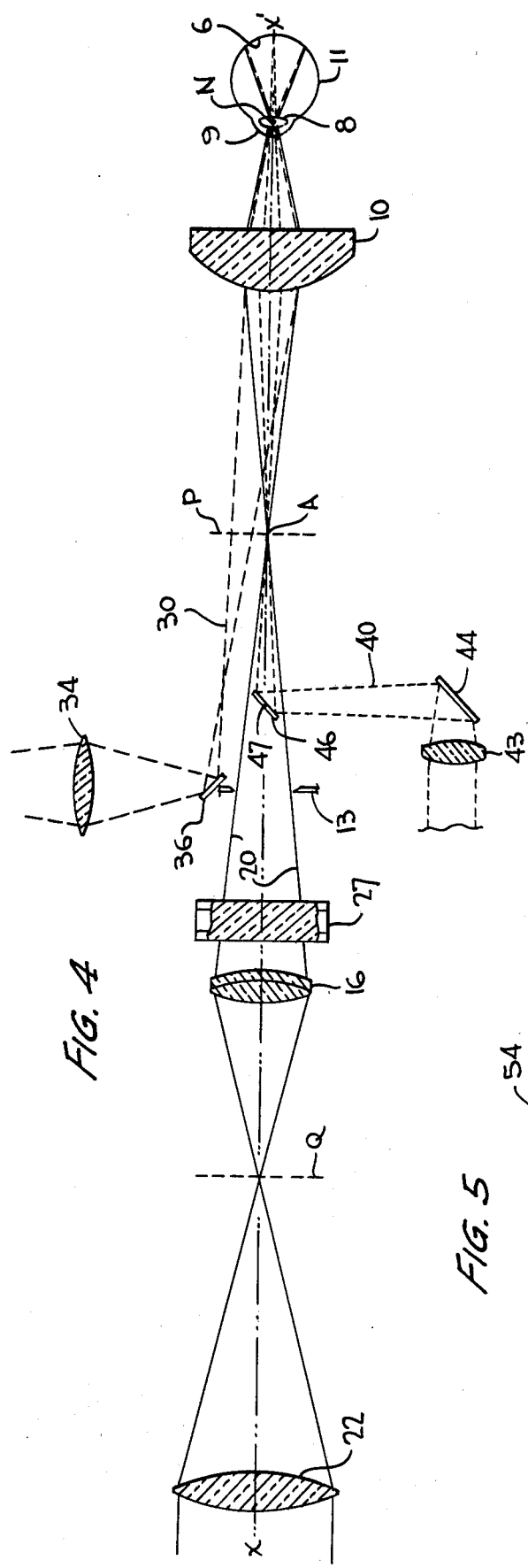
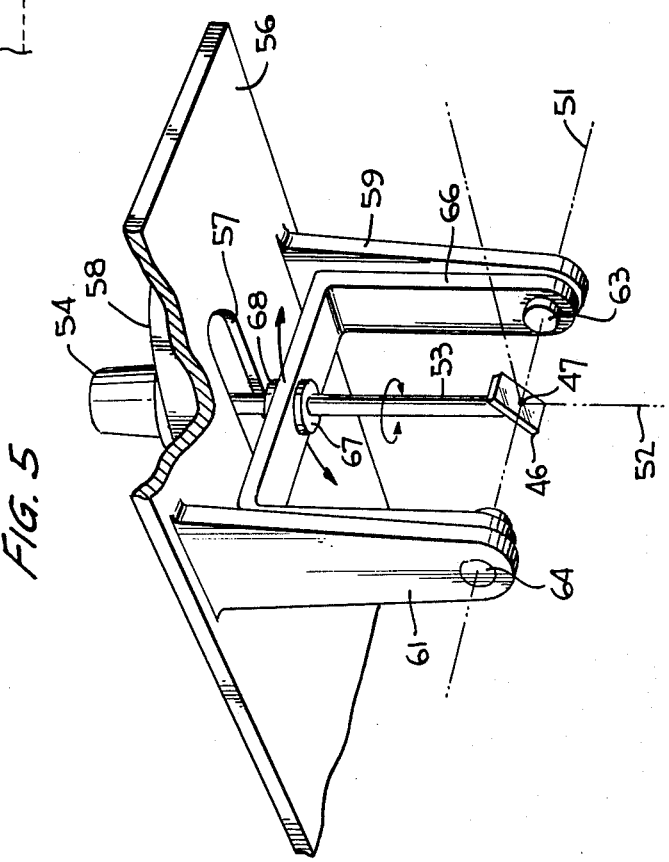

ANASTIGMATIC HIGH MAGNIFICATION, WIDE-ANGLE BINOCULAR INDIRECT ATTACHMENT FOR LASER PHOTOCOAGULATOR

TECHNICAL FIELD

The present invention relates to photocoagulation of the human eye and, more particularly, to improved methods and apparatus for laser photocoagulation.

BACKGROUND OF THE INVENTION

There are numerous prior art photocoagulation systems described in the prior art. Examples of these may be found in the U.S. patents corresponding to the following U.S. Pat. Nos. 2,930,379 (Dopp, et al.); 3,096,767 (Gresser, et al.); 3,467,099 (Lotmar); 3,348,547 (Kavanagh); 3,456,651 (Smart); 3,487,835 (Koester, et al.); 3,720,213 (Hobart, et al.); 3,783,874 (Koester, et al.); 3,809,092 (Abraham); 3,930,504 (de Laforcade); and 3,982,541 (L'Esperance). In all of these patents, a laser beam is disclosed as being directed through the pupil of a patient's eye to be concentrated upon selected areas of the fundus. The laser beam is directed by means of a mirror which rotates or oscillates so as to direct the reflected laser beam accordingly. The laser beam may be directly incident upon the cornea or upon a contact lens placed over the cornea. When oscillated by the oscillating mirror, the laser beam hits the cornea or contact lens at different incidence angles. Under such circumstances, a certain amount of astigmatism is introduced into the laser beam in an amount determined by the angle of incidence. This astigmatism changes to distribution and the density of the energy in the laser beam, resulting in irregularities in the photocoagulation procedure.

In those photocoagulation systems employing a contact lens over the cornea, another problem results. Specifically, it is difficult, when using the contact lens, to achieve the proper depth of focus on the fundus of the eye.

The prior art systems which employ direct ophthalmoscope observation techniques (such as Smart, Kavanagh, Dopp, et al., Gresser, et al., de Laforcade) provide sufficient magnification of the image of the patient's fundus as viewed by the operator. However, the field is very small and there is no stereoscopic viewing. In the Koester, et al. patents, monocular indirect ophthalmoscopic viewing is employed and provides a somewhat larger field, but no stereoscopic viewing and very low magnification.

SUMMARY OF THE INVENTION

It is therefore an object of the present invention to provide a laser photocoagulation apparatus and method which avoids the problem of astigmatism introduced into the laser beam by the scanning mirror. It is a further object of the present invention to provide a laser photocoagulation system and method wherein depth of focus problems are overcome.

It is still another object of the present invention to provide an improved laser photocoagulator system wherein observation is binocular, the observed field is increased by employing a high power objective lens, and magnification is increased by a telescopic system.

In accordance with the present invention, the scanning mirror for the laser beam is disposed with respect to an ophthalmoscopic lens such that the center of the mirror and the nodal point of the crystalline lens in the patient's eye are conjugate points. With this positioning, the laser beam hits the cornea at normal incidence for all positions of the mirror and the laser beam always passes through the nodal point of the patient's eye, resulting in negligible, if any, astigmatism. Further in accordance with the present invention, the contact lens of conventional laser photocoagulation systems is eliminated and the optics of the patient's eye are used to focus the laser beam on the retina. In addition, the main ophthalmoscopic lens is utilized as the primary focusing device and fixes the location of the first retinal image, thereby permitting pre-focusing of the laser beam at this point so that any focusing adjustments for a patient's refraction do not change the focusing of the laser beam spot on the retina.

BRIEF DESCRIPTION OF THE DRAWINGS

The above and still further objects, features and advantages of the present invention will become apparent upon consideration of the following detailed description of one specific embodiment thereof, especially taken in conjunction with the accompanying drawings.

FIG. 1 is a diagrammatic representation of the observation system, viewed from above, of the photocoagulator of the present invention;

FIG. 2 is a diagrammatic side view of the observation system of FIG. 1;

FIG. 3 is a diagrammatic side view of the illumination and laser beam delivery systems of the photocoagulator system of the present invention;

FIG. 4 is a diagrammatic side view of portions of the observation, illumination, and laser beam delivery systems of the photocoagulator of the present invention; and FIG. 5 is a view in perspective of the laser beam scanning mirror and its controls which are employed in the photocoagulator of the present invention.

DESCRIPTION OF THE PREFERRED EMBODIMENT

Referring specifically to FIGS. 1 and 2 of the accompanying drawings, the observation system for a photocoagulator in accordance with the present invention includes an opthalmoscopic objective lens 10 disposed on the optical axis X—X' of a patient's eye 11 so that lens 10 forms the first aerial image of the patient's fundus at a fixed location A. The distance between point A and the patient's eye 11 along axis X—X' is fixed by adjustment of lens 10. This lens is used, not only for the observation system, but also for the illumination and laser beam delivery systems, in the manner described below. Therefore, a single element aspheric lens is utilized for lens 10 to avoid reflections which might be caused by multiple surfaces in a lens composed of several elements. Lens 10 is the only element in the binocular observation system which is common to both eyes of the observer. The fundus image of an emmetropic is focused by lens 10 at point A in the focal plane P of lens 10. This aerial image is refocused by lens 14 (for the left eye) and lens 16 (for the right eye) in plane Q on respective diaphragms 17 and 18 which serve as the field stops of the observation system. The image from plane Q is transmitted via lenses 19 and 21 (for the left eye) in sequence and lenses 22 and 23 (for the right eye) in sequence, to be focused at plane R. The image focused in plane R is viewed by the observer through the oculars 24 and 26 of the system. The stops 12 and 13 of the observation system are located so as to conjugate points with the pupil of the patient's eye 11. The image of stops 12 and 13 focused by lens 10 form the entrance pupils of the observation system. The magnification of the image at plane P for an emmetropic eye of about +60D is approximately 1.8.

A prism 27 is disposed between the stops 12, 13 and the lenses 14, 16 to converge the axes of both observation paths to the axial point A of the first retinal image at plane P of lens 10.

In a particular example, the power of lenses 14, 16 is +50D, the power of lenses 19, 22 is +33D, and the power of lenses 21, 23 is +6.25D. Under such circumstances, the magnification of the ophthalmoscope is 8 times. A different magnification can be obtained by changing the oculars 24, 26. Since the image of the patient's fundus is imaged 5 times (prior to lens 10, plane P, plane Q, plane R, and at the observer), the fundus as viewed, is inverted.

As noted above, prism 27 converges the axes of the observation paths to point A. The separation between the axes of the two observation beams, importantly, is chosen to permit mirrors for the illumination system and laser beam delivery system, as described below, between these two paths.

Referring to FIG. 3, the illumination system includes a bundle of optic fibers 31 which, nominally, is 3 mm in diameter. The optic fibers are illuminated at one end by an optical source (not shown) (such as a varian xenon arc bulb). The light beam emitted by the fiber optic bundle 31 is collimated by condensor 32 and then passed through an adjustable diaphragm 33 and orientable slit 35 to a focusing lens 34. The illumination beam focused by lens 34 is reflected by mirror 36 which is positionally fixed to reflect the illuminating beam 30 toward lens 10. The size of the image of the illuminating source on the patient's pupil is no larger than 3 mm in diameter This means that the solid angle of the light beam focused into the patient's pupil has a total angular aperture of approximately 40°. Therefore, the total ratio of magnification between the tip of the optic fiber bundle and its image in the patient's pupil is 1, and the angular aperture of the light condensor 32 is approximately 40°. Lens 10 focuses the illuminating beam 20 in the patient's pupil with a magnification of 0.25 times.

The laser beam delivery system includes a laser (not shown) of the CW (continuous wave) type conventionally used for photocoagulation of the eye. The beam 40 emitted by this source is passed through a rotatable Galilean telescope system 41 to permit adjustment of the size of the retinal image of the laser beam. Laser beam 40 is passed through a prism 42 which is adjustable for beam diameter striking the cornea 9 of the patient's eye. The laser beam is then passed through a lens 43, which is adjustable for refraction at the patient's eye 11, to a fixed mirror 44. Mirror 44 is positioned to reflect the laser beam onto an adjustable mirror 46. The laser beam 20 reflected from mirror 46 is imaged on the image plane P and, therefore, on the patient's retina 6. The center 47 of mirror 46 is disposed at a point which is conjugate with the nodal point N in the crystalline lens 8 of the patient's eye 11. In a manner to be described below in relation to FIG. 5, mirror 46 is rotatable about both vertical and horizontal axes with center point 47 of the mirror remaining fixed and unaffected by either rotation. This arrangement permits the laser beam to be directed into any location within the field of the observer's view. It strikes different portions of lens 10, but since the center 47 of mirror 46 is at a point which is conjugate with nodal point N of the patient's eye, in any orientation, the axis of the laser beam always passes through this nodal point N. Therefore, in its different orientation, laser beam 20 oscillates about the nodal point of the patient's eye. In all of its orientations, the laser beam 20 is substantially perpendicular to the corneal surface 9.

It is important that both the laser beam scanning mirror 46 and the illumination beam reflecting mirror 36 be disposed with their center points in the vertical plane passing through optical axis X—X'. This feature is best illustrated in FIG. 1. As further noted from FIG. 2, the center point 47 of laser beam delivery mirror 46 is disposed directly on axis X—X'. The reflecting mirror 36 for the observation system, however, may be above or below axis X—X', depending upon the position of the other components in the observation system. The orientation of mirrors 36 and 46 relative to the observation system is also illustrated in FIG. 4 where elements described in relation to FIGS. 1, 2, and 3 bear the same reference numerals utilized in those figures. The observation beam 20 from the two ocular paths are shown focused at point A in the plane P of the first aerial image of the fundus. The observation beams are shown in solid line in FIG. 4. The illumination beam 30, shown in dashed lines in FIG. 4 is shown focused on the patient's pupil by the combined effect of lens 34 in the illumination system and the common ophthalmoscopic lens 10. The laser beam 40, shown with shorter dashes or in dotted form in FIG. 4, is shown focused at point A in plane P and again at the nodal point N in the eye 11 of the patient.

As noted above, it is an important aspect of the present invention that the center 47 of mirror 46 in the laser beam delivery path be stationary at a point which is conjugate with the nodal point N in the patient's eye. A mirror mounting apparatus for permitting mirror 46 to be rotated about both horizontal axis 51 and vertical axis 52 is illustrated in detail in FIG. 5. Specifically, mirror 46 is shown secured to the end of a shaft 53 at the mirror center 47. The other end of shaft 53 is provided with a knob 54, or the like, secured thereto to permit movement by hand of mirror 46 in the manner described subsequently. Shaft 53 is coaxially disposed with vertical axis 52 about which mirror 46 rotates. A support plate 56 is disposed above mirror 56 and has a longitudinally extending slot 57 defined therethrough. Plate 56 is substantially horizontal and slot 57 extends substantially perpendicular to the vertical plane passing through the horizontal axis 51 about which mirror 46 is rotatable. Plate 56 includes a boss 58 extending from its upper surface and through which slot 57 likewise extends. A pair of support arms 59, 61 depend from the bottom surface of plate 56 at locations which are horizontally spaced. A pair of pivot pins 63, 64 extend through suitably provided holes proximate the lower ends of respective arms 59, 61. The pivot pins 63, 64 are concentrically disposed about the horizontal axis 51 about which mirror 46 rotates. It is to be noted that the center 47 of mirror 46 resides on this horizontal axis 51. A U-shaped support member 66 is pivotally mounted at the extremity of each of its legs on respective support pins 63, 64 and is positioned in inverted orientation so that the base portion of the member (i.e. the closed end) is oriented above its open end. Shaft 53 extends through a suitably provided opening in the closed end of member 66 which is provided with journal members 67, 68 to permit rotation of shaft 53 about its longitudinal axis. Members 67, 68 preclude vertical movement of shaft 53 and, in fact, preclude any movement of the shaft 53, relative to member 66, other than the rotation about the longitudinal axis of the shaft. Shaft 53 extends beyond member 66, through slot 57 and boss 58 such that knob 54 is disposed, with considerable clearance, above the boss.

In operation, an operator grabs knob 54 and either rotates shaft 53 about its longitudinal axis or pushes the shaft through slot 57. When the shaft is rotated about its longitudinal axis, mirror 46 rotates therewith without removing center 47 of mirror 46 from its fixed position. When shaft 53 is pushed through slot 57, member 66 pivots about pivot pins 63, 64, causing mirror 46 to rotate about horizontal axis 51. Again, center 47 of mirror 46 remains stationary at the junction of axes 51 and 52. This stationary position of mirror 47, at the point which is conjugate with nodal point N in the patient's eye 11 is the crucial positioning feature of mirror 46 which permits the laser beam to pass through the nodal point N and thereby avoid astigmatism.

It will also be noted from FIGS. 3 and 4 that the absence of a contact lens on eye 11 results in the crystalline lens 8 of the patient's eye being utilized as the lens which focuses the laser beam on the patient's fundus. It is therefore not necessary to provide compensation for variations produced by a contact lens in the depth of focus of the laser beam.

The use of a binocular observation system provides stereoscopic viewing (i.e. stereopsis) whereby the observer can more accurately perceive variations in depth in the eye as viewed. Further, the observed field is increased by utilizing a high-power objective lens 10, and the magnification is increased by utilizing a magnification lens system including lens 14, 19, and 21 and lenses 16, 22, and 23 for the right eye.

In use, assume that the apparatus as described is mounted on a photocoagulator delivery system. The operator first turns on the viewing lamp for the observation system whereby observation beam 30 illuminates the patient's fundus. The operator then adjusts the redicals on the oculars 24, 26 to his/her focus, places the subject in front of the apparatus, so that the eye 11 is on optical axis X—X' and viewed through lens 10 and looks into the eye 11. Lens 10 is adjusted and the location of the first aerial image at plane P is fixed. An emmetropic eye automatically focuses the laser beam on the retina when the laser beam is prefocused at plane P. Note that the use of lens 10 as a focusing device permits prefocusing of the laser beam at plane P so that any focusing adjustments for the patient's refraction do not change the focusing of the laser beam on the retina. The focusing knob would generally be calibrated in diopters which indicate the patient's refractive error. Beyond this ±four diopters, a correction must be utilized for accurate spot size. Changes of spot size are obtainable by a corresponding change of laser beam divergance by using the Galilean telescope system 41. The power and time of exposure of the laser beam are pre-set, as is conventional, and the spot size of the beam is set by the laser beam delivery optics. As is conventional in laser photocoagulation, the laser beam is introduced into the eye at a low power level in order to permit beam adjustment and the laser beam image is positioned by appropriately rotating or moving shaft 53. When the beam image on the fundus is properly positioned, full laser power is introduced to effect photocoagulation.

The laser photocoagulation system described above optimizes instrumentation and reduces inaccuracy in continuous-wave laser systems by solving problems caused by astigmatism of the laser beam and depth of focus of the laser delivery system. Astigmatism of the laser beam is overcome by elimination of the contact lens and by having the laser beam oscillate around the nodal point of the patient's eye. Depth of focus problems are overcome by eliminating the contact lens and utilizing the optics of the patient's eye to focus the beam on the retina.

While I have described and illustrated various specific embodiments of my invention, it will be clear that variations of the details of construction which are specifically illustrated and described may be resorted to without departing from the true spirit and scope of the invention as defined in the appended claims.

I claim:

1. Apparatus for improving photocoagulation of the fundus area of a patient's eye by means of a laser beam introduced into the eye via the pupil of the eye, the eye having a crystalline lens with an optical nodal point, said apparatus including:
   an observation system for viewing the patient's eye along an optical axis passing through said nodal point;
   a laser beam delivery system for directing the laser beam into the pupil of said eye;
   an ophthalmoscopic lens centered on said optical axis and constituting part of both said observation system and said laser beam delivery system;
   wherein said laser beam delivery system includes a scanning mirror rotatable about a fixed point on said optical axis to move an image of said laser beam along said fundus area, said mirror being positioned such that said fixed point and said nodal point are conjugate points of said ophthalmoscopic lens.

2. The apparatus according to claim 1 wherein said ophthalmoscopic lens is the only lens disposed between itself and the patient's eye, whereby the crystalline lens of the patient's eye focuses the laser beam on the fundus area.

3. The apparatus according to claim 2 wherein said observation system is a binocular system having separate viewing paths for two eyes of an observer, which viewing paths employ said ophthalmoscopic lens in common and converge at the plane of the first aerial image of the fundus of the patient's eye produced by said ophthalmoscopic lens.

4. The apparatus according to claim 3 wherein said scanning mirror is disposed between said two viewing paths.

5. The apparatus according to claims 3 or 4 wherein each of said viewing paths includes its own plurality of magnifying lenses disposed along said path.

6. The apparatus according to claims 3 or 4 further comprising an illumination system for directing an illumination beam of light through said ophthalmoscopic lens and the pupil of the patient's eye to illuminate a portion of the fundus of the patient's eye, said illumination system including an illumination mirror for deflecting said illumination beam toward said ophthalmoscopic lens, said illumination mirror being vertically displaced from said optical axis and horizontally disposed between said two viewing paths.

7. The apparatus according to claim 6 further comprising means for permitting independent rotation of said scanning mirror about vertical and horizontal axes while maintaining said fixed point stationary.

8. The apparatus according to claim 1 further comprising an illumination system for illuminating the fundus of the patient's eye through the pupil thereof with an illumination beam, said illumination system including said ophthalmoscopic lens as part thereof.

9. The apparatus according to claim 1, further comprising means for permitting independent rotation of said scanning mirror about vertical and horizontal axes while maintaining said fixed point stationary.

10. Method for improving photocoagulation of the fundus area of a patient's eye by means of a laser beam introduced into the eye via the pupil of the eye, the eye having a crystalline lens with optical nodal point, said method comprising the steps of:
viewing the patient's eye along an optical axis passing through said nodal point and an ophthalmoscopic lens centered on said optical axis;
directing the laser beam into the pupil of said eye through said ophthalmoscopic lens by means of a mirror rotatable in at least two dimensions about a fixed point on said optical axis, said mirror being located with respect to said ophthalmoscopic lens such that said nodal point and said fixed point are conjugate points of said ophthalmoscopic lens.

11. The method according to claim 10 further comprising the step of illuminating the fundus of said patient's eye by passing an illuminating beam through the pupil of the patient's eye via said ophthalmoscopic lens.

12. The method according to claims 10 or 11 wherein said step of viewing the patient's eye includes binocular viewing along two separate paths which converge at the first aerial image of the patient's fundus provided by said ophthalmoscopic lens.

13. The method according to claim 12 wherein said step of directing the laser beam includes focusing the laser beam in the plane of said first aerial image.

14. The method according to claim 10 wherein said step of viewing the patient's eye includes binocular viewing of a patient's eye along two separate viewing paths and wherein said fixed point is disposed between said viewing paths.

* * * * *